United States Patent
Clabeaux (12)

(10) Patent No.: US 10,894,156 B2
(45) Date of Patent: Jan. 19, 2021

(54) IMPLANTABLE MEDICAL DEVICES HAVING RESILIENT MOUNTING TABS AND ASSOCIATED METHODS

(71) Applicant: ADVANCED BIONICS AG, Staefa (CH)

(72) Inventor: Sarah Elizabeth Clabeaux, Ventura, CA (US)

(73) Assignee: Advanced Bionics AG, Staefa (CH)

( * ) Notice: Subject to any disclaimer, the term of this patent is extended or adjusted under 35 U.S.C. 154(b) by 249 days.

(21) Appl. No.: 15/961,711

(22) Filed: Apr. 24, 2018

(65) Prior Publication Data

US 2018/0236250 A1    Aug. 23, 2018

Related U.S. Application Data

(63) Continuation-in-part of application No. PCT/US2015/059270, filed on Nov. 5, 2015.

(51) Int. Cl.
| | | |
|---|---|---|
| *A61N 1/375* | (2006.01) | |
| *A61N 1/05* | (2006.01) | |
| *A61N 1/36* | (2006.01) | |
| *H04R 25/00* | (2006.01) | |

(52) U.S. Cl.
CPC ....... *A61N 1/0541* (2013.01); *A61N 1/36038* (2017.08); *A61N 1/37518* (2017.08); *H04R 25/604* (2013.01)

(58) Field of Classification Search
CPC ................................................. A61N 1/36038
See application file for complete search history.

(56) References Cited

U.S. PATENT DOCUMENTS

| | | | |
|---|---|---|---|
| 5,249,574 A | 10/1993 | Bush et al. | |
| 6,078,841 A | 6/2000 | Kuzma | |
| 7,881,800 B2 | 2/2011 | Daly et al. | |
| 8,489,195 B2 | 7/2013 | Dalton et al. | |
| 2003/0125739 A1 | 7/2003 | Bagga et al. | |
| 2006/0004364 A1* | 1/2006 | Green | A61B 17/0642 606/232 |
| 2006/0116743 A1 | 6/2006 | Gibson et al. | |
| 2008/0195178 A1* | 8/2008 | Kuzma | A61N 1/375 607/57 |
| 2009/0248054 A1* | 10/2009 | Sage | A61M 25/02 606/174 |
| 2011/0208303 A1 | 8/2011 | Gibson | |
| 2012/0296444 A1 | 11/2012 | Greenberg et al. | |
| 2014/0046395 A1 | 2/2014 | Regnier et al. | |

(Continued)

FOREIGN PATENT DOCUMENTS

AU    2013263808 B2    12/2013

OTHER PUBLICATIONS

PCT International Search and Written Opinion dated Feb. 10, 2016 for PCT App. Ser. No. PCT/US2015/059270.

*Primary Examiner* — Rex R Holmes
*Assistant Examiner* — Jennifer L Ghand
(74) *Attorney, Agent, or Firm* — Henricks Slavin LLP (57) ABSTRACT

A method, for use with an implantable medical device, including the steps of stretching a mounting tab in such a manner that an aperture on the mounting tab increases in size and separating the mounting tab from a bone anchor by moving the stretched mounting tab in such a manner that the bone anchor does not extend through the aperture in the mounting tab.

16 Claims, 6 Drawing Sheets

(56) References Cited

U.S. PATENT DOCUMENTS

| | | | |
|---|---|---|---|
| 2015/0146902 A1 | 5/2015 | Jinton et al. | |
| 2015/0164498 A1* | 6/2015 | Dreyfuss | A61B 17/0401 |
| | | | 606/229 |
| 2019/0099173 A1 | 4/2019 | Ladurner et al. | |
| 2019/0336752 A1* | 11/2019 | Bauer | A61N 1/0539 |

* cited by examiner

IMPLANTABLE MEDICAL DEVICES HAVING RESILIENT MOUNTING TABS AND ASSOCIATED METHODS

CROSS-REFERENCE TO RELATED APPLICATIONS

This application is a continuation-in-part of, and claims priority to, International Application No. PCT/US2015/059270, filed Nov. 5, 2015, which is incorporated herein by reference in its entirety.

BACKGROUND

1. Field

The present disclosure relates generally to implantable medical devices such as, for example, the implantable portion of implantable cochlear stimulation systems.

2. Description of the Related Art

A wide variety of medical devices may be implanted within a patient and secured to a portion of the body (e.g., bone or other tissue) to prevent post implantation movement of the medical device. Although the present inventions are not so limited, one such implantable device is an implantable cochlear stimulator (or "cochlear implant"), and the present inventions are described primarily in the context of cochlear implants. Other exemplary implantable medical devices include, but are not limited to, cardiac pacemakers, defibrillators, recording devices, neuromuscular stimulators, drug infusion pumps and deep brain stimulators.

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array is carried on a lead that has been inserted into the cochlea of the inner ear, and electrical stimulation current is applied to varying electrode combinations to create a perception of sound. The electrode array may, alternatively, be directly inserted into the cochlear nerve without residing in the cochlea.

Some ICS systems include a cochlear implant, a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

Various techniques may be employed to prevent movement of medical devices after they have been surgically implanted. In the exemplary context of cochlear implants, such techniques include drilling a bone bed into the skull in the shape of the cochlear implant, drilling bone anchors into the skull and using the bone anchors to anchor sutures that extend over the implant, forming a tight pocket for the device in the periosteum, and drilling bone screws through one or more portions of the implant and into the skull. The present inventor has determined that these conventional techniques are susceptible to improvement. With respect to drilling bone beds, this technique significantly extends the duration of the associated surgical procedure, requires a unique sizing gauge for each implant device, requires a great deal of surgical skill, and is especially difficult in the pediatric context due to the thinness of the skull. Suturing across the implant from one anchor to another is also quite time consuming and the suture ends can sometimes become irritants. Tight pockets do not always prevent implant migration. With respect to bone screws that extend through the implant, the bone screws tend to become permanently integrated into the bone, which can be problematic should implant removal become necessary. Here, the bone screws must be drilled out of the bone and, when the removed implant (or a replacement implant) is subsequently implanted, the new bone screws must be offset from the prior bone screw locations. As a result, the cochlear implant, including the lead that carries the electrode array, must be repositioned.

SUMMARY

A method in accordance with one of the present inventions may be used in conjunction with an implantable medical device that is secured to a tissue structure of a patient by an anchor that passes through an aperture in a mounting tab at least a portion of which is resilient (referred to herein as a "resilient mounting tab"), and into the tissue structure. The method may include the steps of stretching the mounting tab in such a manner that the aperture increases in size and separating the resilient mounting tab from the anchor.

An implantable medical device for use with an anchor, having a post and a head that is larger than the post, which is secured to a tissue structure, the implantable medical device including an operative portion and at least one mounting tab associated with the operative portion and having an aperture that is configured to receive the post, at least a portion of the mounting tab being configured to stretch, in a first direction without tearing, from a first size where the aperture is smaller than the anchor head to a second size that is larger than the first size in the first direction and that allows the aperture to fit over the anchor head. In some instances, the implantable medical device may be a cochlear implant. The present inventions also include systems with such a cochlear implant in combination with a sound processor.

There are a number of advantages associated with such methods and apparatus. For example, an implanted and anchored medical device (such as a cochlear implant) may be readily disconnected from one or more anchors (such as bone screws) and removed from the patient without removing, adjusting or replacing the anchors.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Implantable medical devices in accordance with the present inventions include an operative portion, which includes components that perform a medical function (e.g., stimulating the cochlea or stimulating heart tissue), and one or more mounting tabs that secure the operative portion to a tissue structure. One example of an implantable medical device is a cochlear implant (or "implantable cochlear stimulator"), and one example of a cochlear implant is the cochlear implant 100 illustrated in FIG. 1. The cochlear implant 100 includes a flexible housing 102 formed from a silicone elastomer or other suitable material, a processor assembly 104, a cochlear lead 106, and an antenna 108 that may be used to receive data and power by way of an external antenna that is associated with, for example, a sound processor unit. The flexible housing 102 includes a processor portion 110 in which the processor assembly 104 is located and an antenna portion 112 in which the antenna 108 is located. The cochlear lead 106 may include a flexible body 114, an electrode array 116 at one end of the flexible body 114, and a plurality of wires (not shown) that extend through the flexible body from the electrodes 118 (e.g., platinum electrodes) in the array 116 to the other end of the flexible body. The exemplary antenna 108 is a coil antenna with one or more loops (or "turns"), and three loops are shown in the illustrated embodiment. The exemplary processor assembly 104, which is connected to the electrode array 116 and antenna 108, includes a printed circuit board 120 with a stimulation processor 122 that is located within a hermetically sealed case 124. The stimulation processor 122 converts stimulation data into stimulation signals that stimulate the electrodes 118 of the electrode array 116.

Figure 1:
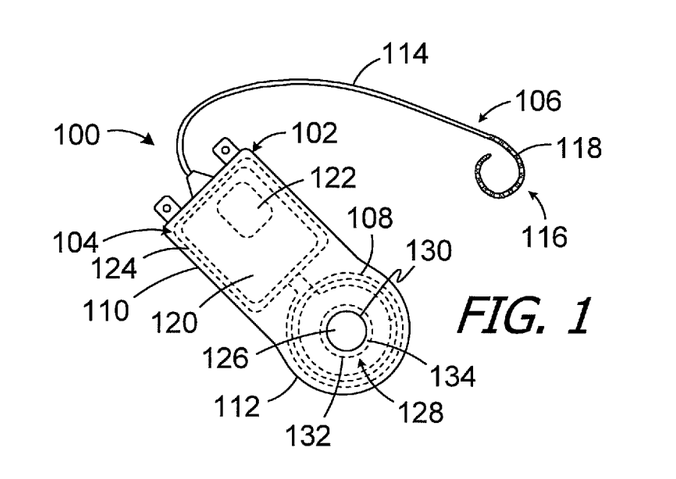
FIG. 1 is a plan view of a cochlear implant in accordance with one embodiment of a present invention.

A positioning magnet 126, which is used to maintain the position of a headpiece transmitter over the antenna 108, is located within the housing 102. It is sometimes necessary to remove the magnet from the cochlear implant, and then reinsert the magnet, in situ, i.e., with the cochlear implant accessed by way of an incision in the skin. To that end, the positioning magnet 126 in the illustrated embodiment is carried within an internal magnet pocket 128 and can be inserted into, and removed from, the housing pocket by way of a magnet aperture 130 that extends through the housing top wall. The magnet 126 is larger than the magnet aperture 130, i.e., the outer diameter of the magnet is greater than the diameter of the magnet aperture. The portion of the top wall between the aperture 130 and the outer edge 132 of the magnet 126 forms a retainer 134 that, absent deformation of the aperture and retainer, prevents the magnet from coming out of the housing 102. During installation and removal, the aperture 130 and retainer 134 are stretched or otherwise deformed so that the magnet 126 can pass through the aperture 130. It should be noted, however, that the present cochlear implants not limited to those that secure a removable magnet in this manner and that other structures for securing a removable magnet may be employed. The present cochlear implants are also not limited to those with removable magnets and, to the contrary, include cochlear implants with non-removable magnets and cochlear implants without magnets.

Figure 2:
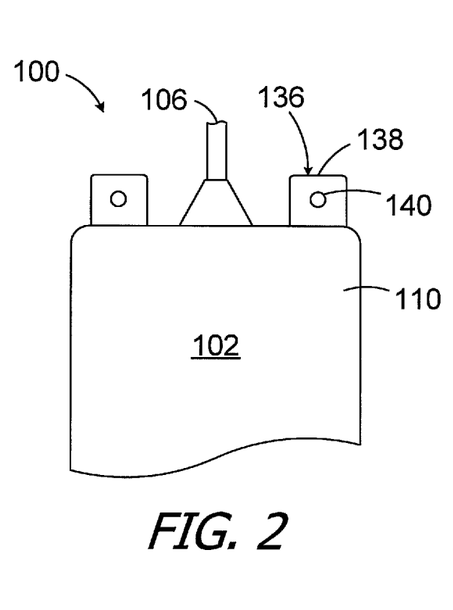
FIG. 2 is a plan view of a portion of the cochlear implant illustrated in FIG. 1.
Figure 3:
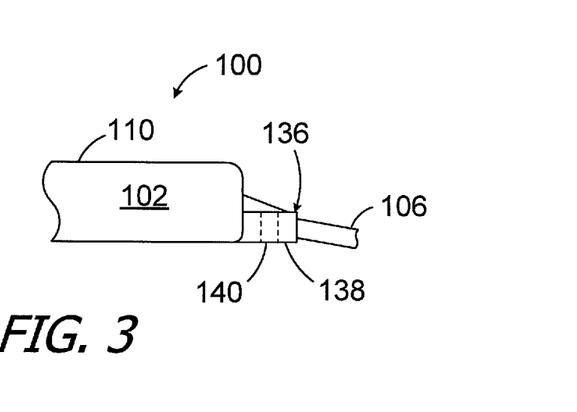
FIG. 3 is a side view of a portion of the cochlear implant illustrated in FIG. 1.

Turning to FIGS. 2 and 3, the exemplary cochlear implant 100 may include one or more mounting tabs 136, and there are two mounting tabs in the exemplary implementation. At least a portion of each exemplary mounting tab 136 is resilient. The mounting tabs 136 may be used in combination with tissue anchors (or "anchors") that are attached to the skull to fix the position of the cochlear implant 100 in such a manner that cochlear implant can disconnected from the anchors and removed if necessary without removing, adjusting or replacing the anchors. The same cochlear implant (or a replacement) may thereafter be reconnected to the same anchors without removing, adjusting or replacing the anchors. The mounting tabs 136 extend outwardly from the housing 102 and, in the exemplary implementation, both mounting tabs extend outwardly from the same end of the housing as the cochlear lead 106. This location facilitates the use of a relatively short incision during the implantation and removal procedures. The mounting tabs 136 each include a tab body 138 and an aperture 140.

In the context of bone tissue, exemplary tissue anchors include, but are not limited to, bone screws (e.g., standard bone screws and self-drilling bone screws) and other devices that have at least a portion which is anchored to bone, such as pins that are glued to the bone. In certain situations where the formation of scar tissue will eventually hold the cochlear implant or other implanted medical device in place at the desired location, tissue anchors which are absorbed into the body after a predetermined period (e.g., six months) may be employed. With respect to tissue other than bone (e.g., a heart wall to which a pacemaker lead is secured), one exemplary anchor that may be used to anchor a medical device to tissue is an absorbable barbed suture with a head.

Figure 4:
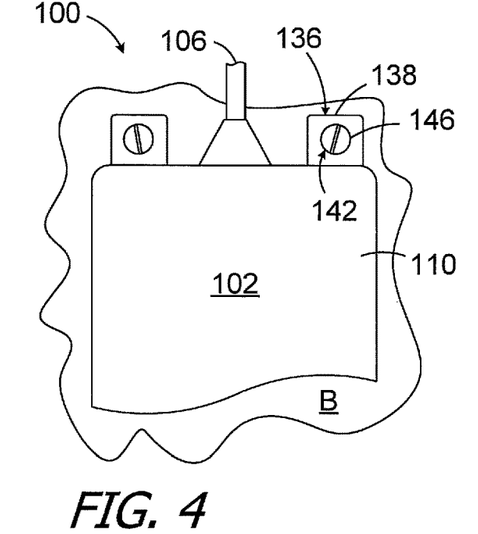
FIG. 4 is a plan view of a portion of the cochlear implant illustrated in FIG. 1 secured to bone.
Figure 5:
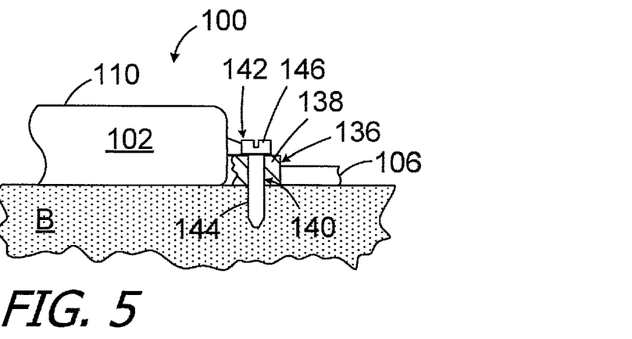
FIG. 5 is a side, partial section view of a portion of the cochlear implant illustrated in FIG. 1 secured to bone.

As illustrated for example in FIGS. 4 and 5, anchors with posts and heads that are larger than the posts, such as bone screws 142, may be used to secure each mounting tab 136 to bone B, thereby fixing the position of the cochlear implant 100. Each bone screw 142 has a shank 144 with a diameter that is similar to the diameter of aperture 140 and a head 146 with a diameter that is larger than the diameter of aperture and the diameter of the shank, as is discussed below. Other exemplary bone screw-type anchors are described below with reference to FIGS. 23A-24. During the initial implantation procedure, the cochlear implant 100 is positioned in the desired location on the patient's skull. The locations of the apertures 140 define the locations of the bone screws 142. The bone screws 142 are inserted into the apertures 140 and driven into the bone B. The thickness of the tab bodies 138 and the length of the shanks 144 may be used to set the depth to which the bone screws 142 will be driven into the bone B. The aperture 140 and an adjacent portion of the tab body 138 are located between the bone B and the bone screw head 146, which secures the resilient mounting tab to the bone screw 142 and to the bone. The position of the cochlear implant 100 is thereby fixed.

Figure 6:
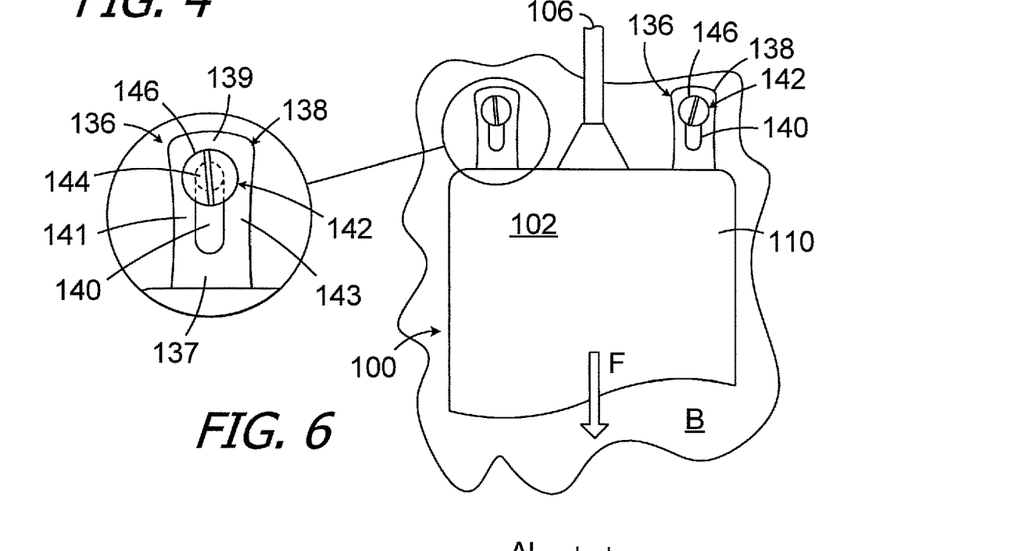
FIG. 6 is a plan view of a portion of the cochlear implant illustrated in FIG. 1 secured to bone with the mounting tabs stretched.
Figure 7:
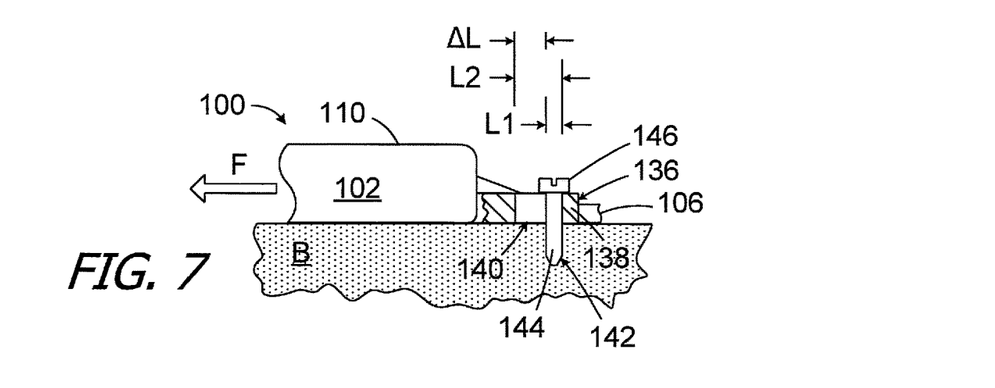
FIG. 7 is a side, partial section view of a portion of the cochlear implant illustrated in FIG. 1 secured to bone with the mounting tabs stretched.

The properties of mounting tabs 136, which are discussed in greater detail below, allow the mounting tabs to be, as noted above, disconnected from bone screws 142 without removing, adjusting or replacing the bone screws, and without tearing the tabs. The resilience of at least the portion of the mounting tabs 136 adjacent to the aperture 140 allows the tabs to stretch, from the state illustrated in FIGS. 4 and 5 to the state illustrated in FIGS. 6 and 7, in response to the application of a force F to the cochlear implant housing 102. Both the tab body 138 and the aperture 140 increase in length when the mounting tab 136 is stretched. The direction of the increase in length corresponds to the direction of the force F such that the tab body 138 has elongated side portions 138a and 138b, on opposite sides of the elongated aperture 140, as well as end portions 138c and 138d. Referring more specifically to FIG. 7, the length of the aperture 140 increases by a length ΔL from its initial length L1 (the unstretched diameter of the aperture 140 in the illustrated embodiment) to a disconnection length L2. The disconnection length L2 is one example of an aperture length which allows the tab body 138 to be maneuvered over the head 146 of the bone screw 142 to separate the mounting tab 136 from the bone screw in the manner described below. The disconnection length L2 need only be long enough to allow the aperture 140 to be maneuvered past the bone screw head 146.

Figure 8:
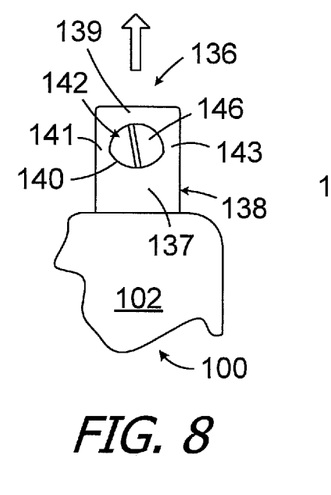
FIG. 8 is a plan view showing a mounting tab partially disconnected from a bone screw.
Figure 9:
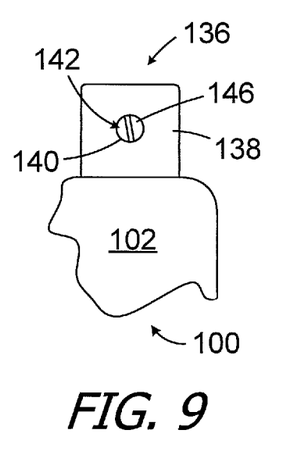
FIG. 9 is a plan view showing a mounting tab disconnected from a bone screw.
Figure 10:
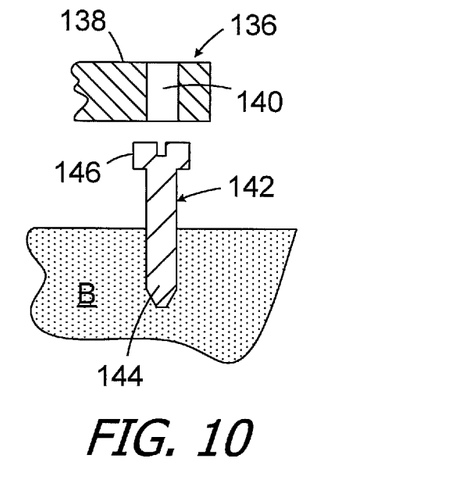
FIG. 10 is a section view showing a mounting tab disconnected from a bone screw.
Figure 11:
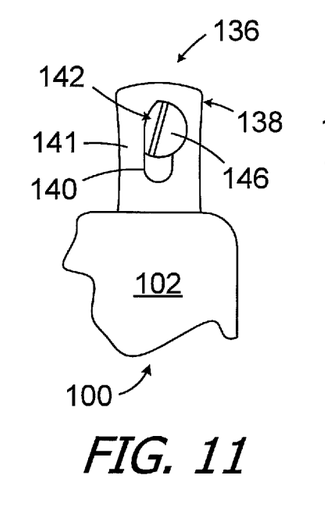
FIG. 11 is a plan view showing a mounting tab partially disconnected from a bone screw.
Figure 12:
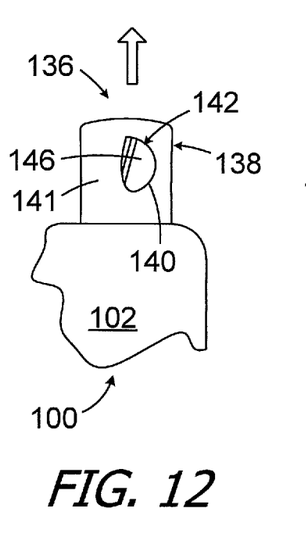
FIG. 12 is a plan view showing a mounting tab partially disconnected from a bone screw.
Figure 13:
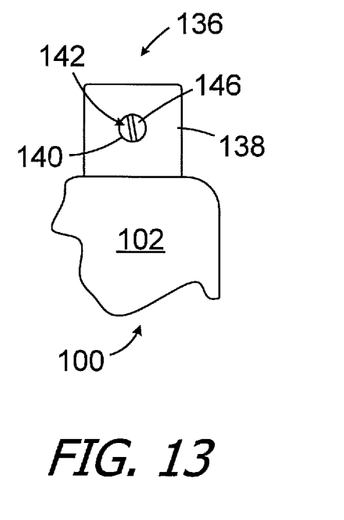
FIG. 13 is a plan view showing a mounting tab disconnected from a bone screw.

After the mounting tab 136 has been stretched, the mounting tab may be lifted, twisted or otherwise maneuvered off associated bone screw 142 (or other anchor) in a variety of ways, both with and without surgical tools and with or without additional movement of the remainder of the cochlear implant 100. By way of example, but not limitation, the base portion 137 (i.e., the portion between the housing 102 and the aperture 140) may be lifted up and over the bone screw head 146 in the manner illustrated in FIG. 8. Continued movement of the mounting tab 136 in the direction of the arrow will allow the side portions 141 and 143 and the tip portion 139 (i.e., the portion between the aperture 140 and the free end of the tab body) clear the screw head 146. The resilience of the mounting tab 136 will then cause the aperture 140 to return to its non-stretched (or unstressed) state as is shown in FIGS. 9 and 10. The bone screw 142 is not removed or otherwise adjusted during this process. Another exemplary removal method is illustrated in FIGS. 11-13. Here, after the mounting tab 136 has been stretched, the stretched side portion 141 is maneuvered up and over the bone screw head 146 (FIG. 11) either directly, with a finger or tool, or indirectly by twisting the cochlear implant housing 102. Movement in the direction of the arrow in FIG. 12, coupled with additional maneuvering and the resilience of the mounting tab 136, will cause the remainder of the mounting tab to move up and over the bone screw head 146. The aperture 140 will then to return to its non-stretched (or unstressed) state illustrated in FIG. 13. The process may then be repeated with the second mounting tab 136 to disconnect the cochlear implant 100 from the bone B without removing or adjusting the bone screws 142.

Figure 14A:
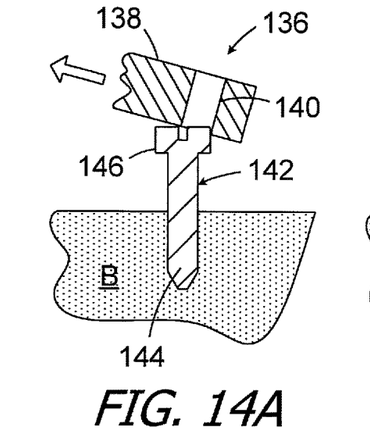
FIG. 14A is a section view showing a mounting tab being connected to a bone screw.
Figure 14B:
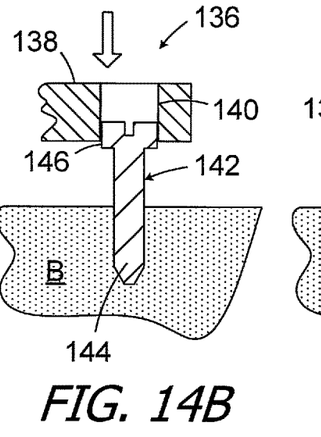
FIG. 14B is another section view showing a mounting tab being connected to a bone screw.
Figure 14C:
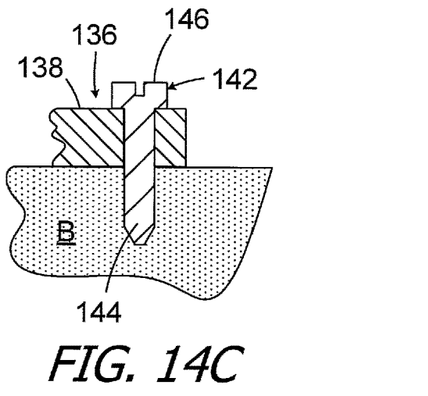
FIG. 14C is a section view showing a mounting tab connected to a bone screw.

A mounting tab 136 may be attached to a bone screw 142, or other anchor, in the exemplary manner illustrated in FIGS. 14A-14C when a previously removed (or new) cochlear implant is implanted. A portion of the aperture 140 is placed over the bone screw head 146 (FIG. 14A) and the mounting tab 136 is stretched in the direction of the arrow to stretch the aperture 140. The mounting tab 136 may then be maneuvered in such a manner that the bone screw head 146 is within the aperture 140 (FIG. 14B), and then pushed toward the bone B in the direction of the arrow. When the aperture 140 passes the bone screw head 146, the resilience of the mounting tab 136 will cause the aperture 140 to return to its non-stretched (or unstressed) state (FIG. 14C), with a diameter that is less than that of the bone screw head 146. At this point, the aperture 140 and an adjacent portion of the tab body 138 are located between the bone B and the bone screw head 146, thereby attaching the mounting tab to the bone screw 142 and securing the mounting tab 136 (and cochlear implant 100) to the bone.

Figure 15A:
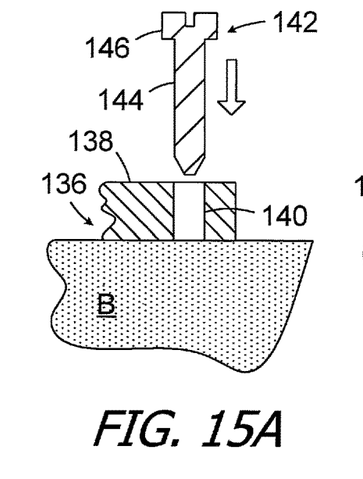
FIG. 15A is a section view showing a mounting tab being connected to a bone screw.
Figures 15B, 15C:
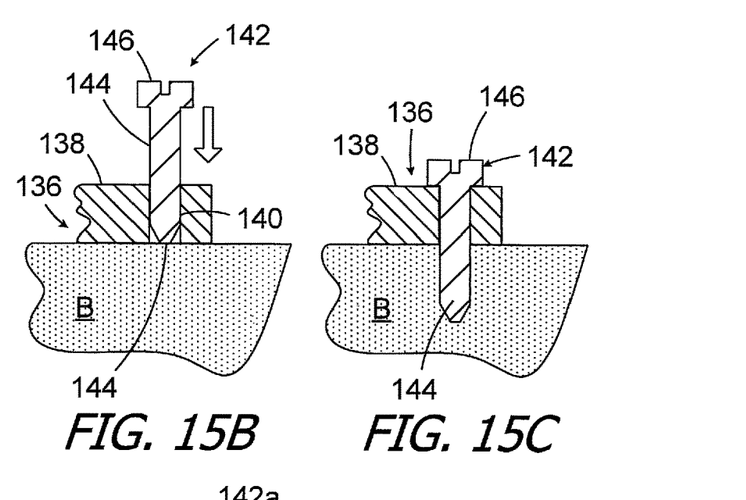
FIG. 15B is another section view showing a mounting tab being connected to a bone screw.
FIG. 15C is a section view showing a mounting tab connected to a bone screw.

A mounting tab 136 may also be attached to a bone screw 142, or other anchor, in the exemplary manner illustrated in FIGS. 15A-15C when a new cochlear implant is implanted. Here, the mounting tab 136A is placed on the bone B prior to being attached to an anchor. The bone screw 142 is then aligned with the aperture 140 (FIG. 15A). The bone screw 142 may then be pushed through the aperture 140 (FIG. 15B) and driven into the bone B. When the bone screw 142 reaches, for example, the location illustrated in FIG. 15C, the aperture 140 and an adjacent portion of the tab body 138 are located between the bone B and the bone screw head 146, thereby attaching the mounting tab 136 to the bone screw 142 and securing the mounting tab (and cochlear implant 100) to the bone.

Figure 16A:
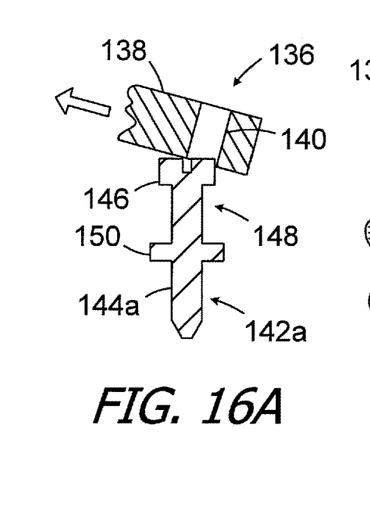
FIG. 16A is a section view showing a mounting tab being connected to a bone screw.
Figures 16B, 16C:
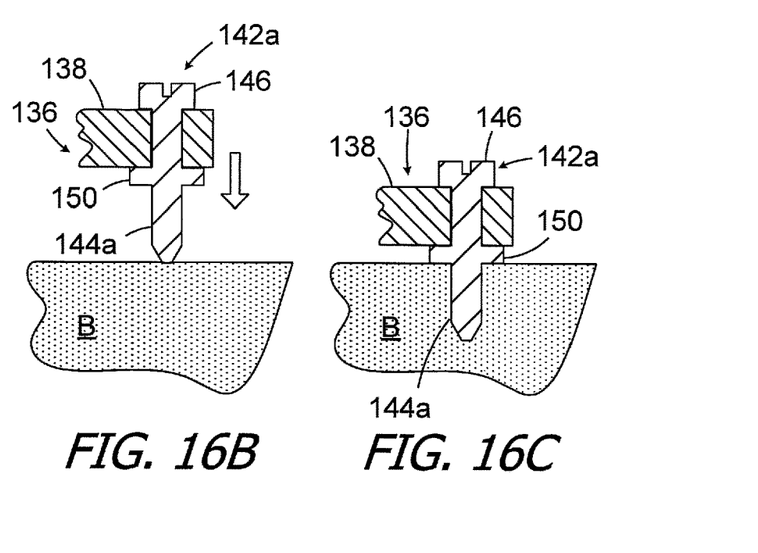
FIG. 16B is a section view showing a mounting tab being connected to a bone screw.
FIG. 16C is another section view showing a mounting tab connected to a bone screw.

A mounting tab 136 may also be attached to a bone screw 142a (discussed below with reference to FIGS. 23A-23B), or other similar anchor, in the exemplary manner illustrated in FIGS. 16A-16C when a new cochlear implant is implanted. A portion of the aperture 140 is placed over the bone screw head 146 (FIG. 16A) prior to the bone screw 142a being anchored into the bone B, and the mounting tab 136 may be stretched in the direction of the arrow to stretch the aperture 140. The mounting tab 136 may then be maneuvered over and past the bone screw head 146 such that the mounting tab is located within the gap 148 between the screw head and the flange 150. The resilience of the mounting tab 136 will cause the aperture 140 to return to its non-stretched (or unstressed) state (FIG. 16B), with a diameter that is less than that of the bone screw head 146 and flange 150. At this point, the mounting tab 136 is attached to the bone screw 142a. The bone screw 142a may then be driven into the bone B (FIG. 16C) to secure the mounting tab 136 (and cochlear implant 100) to the bone. A wide variety of mounting tab shapes, dimensions and materials may be employed so long as the resulting mounting tab is configured to function in the manner described above. Exemplary aspects that, taken in combination, result in a mounting tab that is configured to function in the manner described above include the tensile strength and tear strength of the mounting tab material, the length, width and thickness of the mounting tab (or at least the portion of the mounting tab that is resilient), and the size and location of the aperture. Certain dimensions may also be a function of dimensions of the anchor. In the exemplary context of a bone screw, the head may be 1.5 to 2 times the diameter of the shank, and the diameter of the mounting tab aperture may be slightly less than, equal to, or slightly greater than the diameter of the shank to create a tight fit, a line-to-line fit, or a loose fit, each of which prevents the mounting tab from being inadvertently dislodged from the associated anchor, while allowing the mounting tab to be removed from the anchor in the manner described above.

The mounting tabs 136 may be integrally molded with, or separately formed from and attached to, the housing 102. Suitable mounting tab materials include, but are not limited to, resilient liquid silicone rubbers such as, for example, SILPURAN® 8020 from Wacker Chemie AG.

Figure 17:
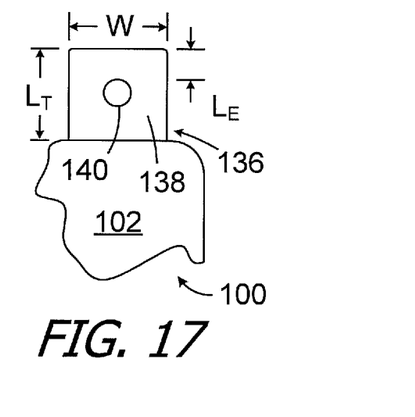
FIG. 17 is a plan view of a portion of the cochlear implant illustrated in FIG. 1.
Figure 18:
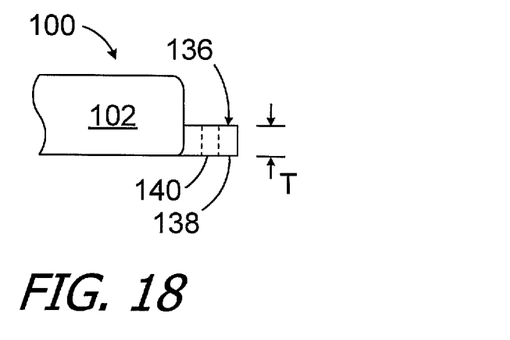
FIG. 18 is a side view of a portion of the cochlear implant illustrated in FIG. 1.
Figure 19:
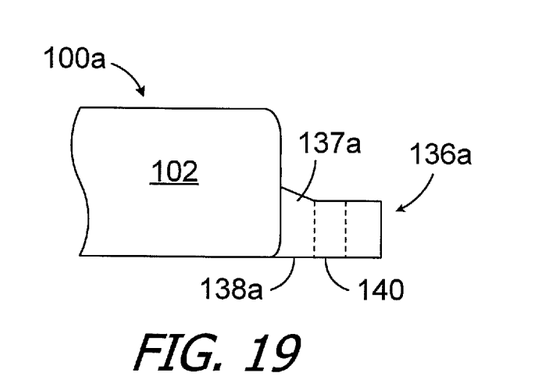
FIG. 19 is a side view of a portion of a cochlear implant in accordance with one embodiment of a present invention.
Figure 20:
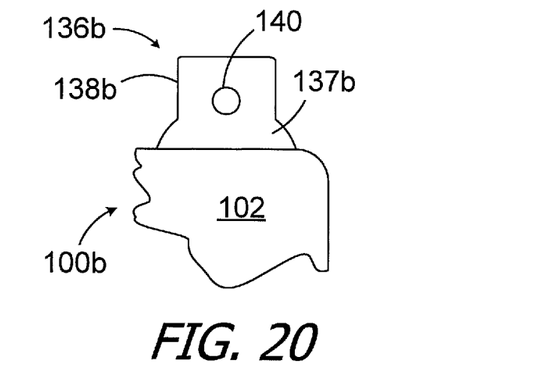
FIG. 20 is a plan view of a portion of a cochlear implant in accordance with one embodiment of a present invention.
Figure 21:
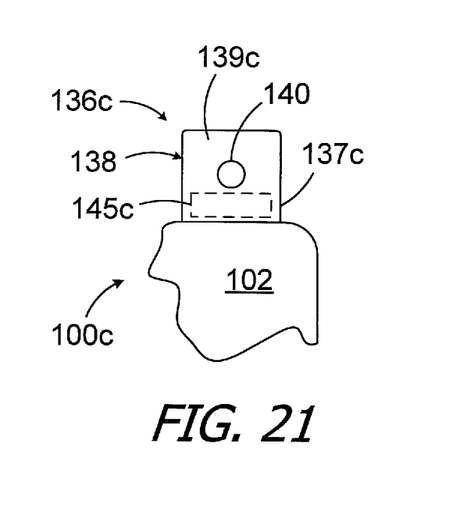
FIG. 21 is a plan view of a portion of a cochlear implant in accordance with one embodiment of a present invention.

Referring to FIGS. 17 and 18, in one exemplary configuration, the mounting tab 136 is formed from a material having a tensile strength of 10 N/mm$^2$ and a tear strength of 28 N/mm. The width W is 5.5 mm, the total length $L_T$ is 5 mm, the end length $L_E$ from the aperture 140 to the free end of the mounting tab is 1.9 mm, the aperture 140 has a diameter of 1.6 mm and is centered in the width direction, and the thickness T is 1.45 mm.

Figure 22:
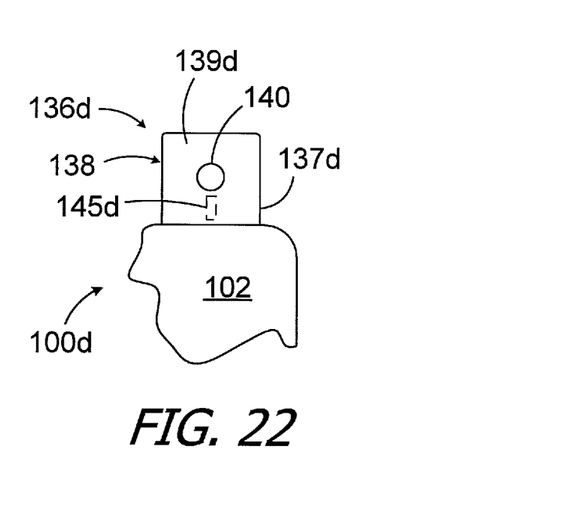
FIG. 22 is a plan view of a portion of a cochlear implant in accordance with one embodiment of a present invention.

The present mounting tabs are not limited to configuration illustrated in FIGS. 1-18. By way of example, but not limitation, cochlear implants 100a-100d illustrated in FIGS. 19-22 are identical to cochlear implant 100, but for the configuration of the mounting tabs 136a-136d, and similar elements are represented by similar reference numerals. For example, the thickness of the mounting tabs may vary over some or all of their lengths. To that end, the exemplary mounting tab 136a in FIG. 19 has a tab body 138a with a base portion 137a having a thickness that decreases from the housing 102 to the aperture 140. The thickness of the remainder of the tab body 138a is constant. Alternatively, or in addition, the width of the mounting tabs may vary over some or all of their lengths. The exemplary mounting tab 136b illustrated in FIG. 20, for example, has a tab body 138b with a base portion 137b that has a width which decreases from the housing 102 to the aperture 140. Structures may also be embedded in or otherwise carried by the mounting tabs to alter the properties of the mounting tabs. Structures that, for example, reduce or eliminate the resiliency of a portion of the mounting tab may be employed. The exemplary mounting tab 136c includes a reinforcing member 145c (e.g., Teflon mesh) in the base portion 137c that, depending on configuration, reduces or eliminates the resilience of the base portion. The portion of the tab body 138c with the aperture 140 remains resilient, as does the tip portion 139c that is located between the aperture 140 and the free end of the tab body. Turning to FIG. 22, the exemplary mounting tab 136d includes a malleable member 145d (e.g., a malleable wire) in the base portion 137d. The malleable member 145d, which will hold its shape after being bent, allows the surgeon to shape the mounting tab base portion 137d in a manner that conforms to the skull or other underlying tissue structure. The portion of the tab body 138d with the aperture 140 and the tip portion 139c will remain resilient. It should also be noted that the present mounting tabs include mounting tabs with any and all combinations of the features in mounting tabs 136a-136d.

Figure 23A:
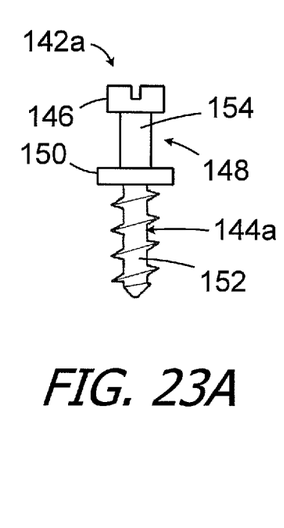
FIG. 23A is a side view of a bone screw.
Figure 23B:
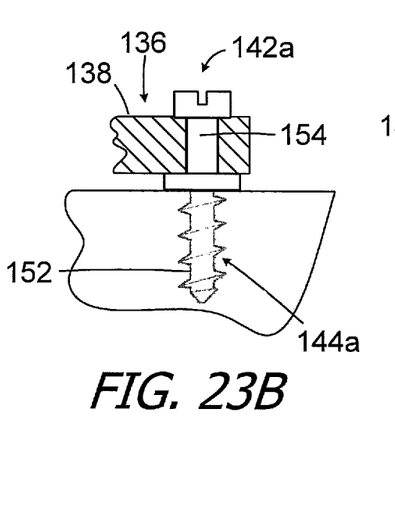
FIG. 23B is a side, partial section view showing a mounting tab connected to a bone screw.

It should also be noted that the configuration of some bone screws reduces the likelihood that the bone screw will damage the associated mounting tab. Referring first to FIG. 23A, the exemplary bone screw 142a has a shank 144a and a head 146, with respective diameters that are the same as (or similar to) those described above, and a gap 148 between the flange 150 and the head. The shank 144a has a threaded portion 152 (i.e., a portion with threads) and a non-threaded portion 154 (i.e., a smooth portion with no threads). The flange 150 is located between the threaded portion 152 and the non-threaded portion 154. The bone screw 142a may be used to secure the mounting tab 136 (and cochlear implant 100) to the bone B in the manner illustrated in FIG. 23B. Here, and as shown in FIG. 23B, the non-threaded portion 154 is in contact with the tab body 138 at the aperture 140. The non-threaded portion 154 is smooth and is less likely to cut, tear or otherwise damage the mounting tab 136 as compared to the threaded portion 152 (or the threads of another bone screw).

Figure 24:
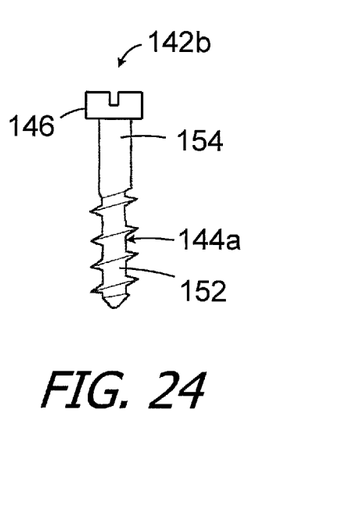
FIG. 24 is a side view of a bone screw.

Another exemplary bone screw that may be used in conjunction with the present cochlear implants is generally represented by reference numeral 142b in FIG. 24. Bone screw 142b is substantially similar to bone screw 142a and similar elements are represented by similar reference numerals. Here, however, there is no flange between the threaded portion 152 and the non-threaded portion 154 of the shank 144a.

Figure 25:
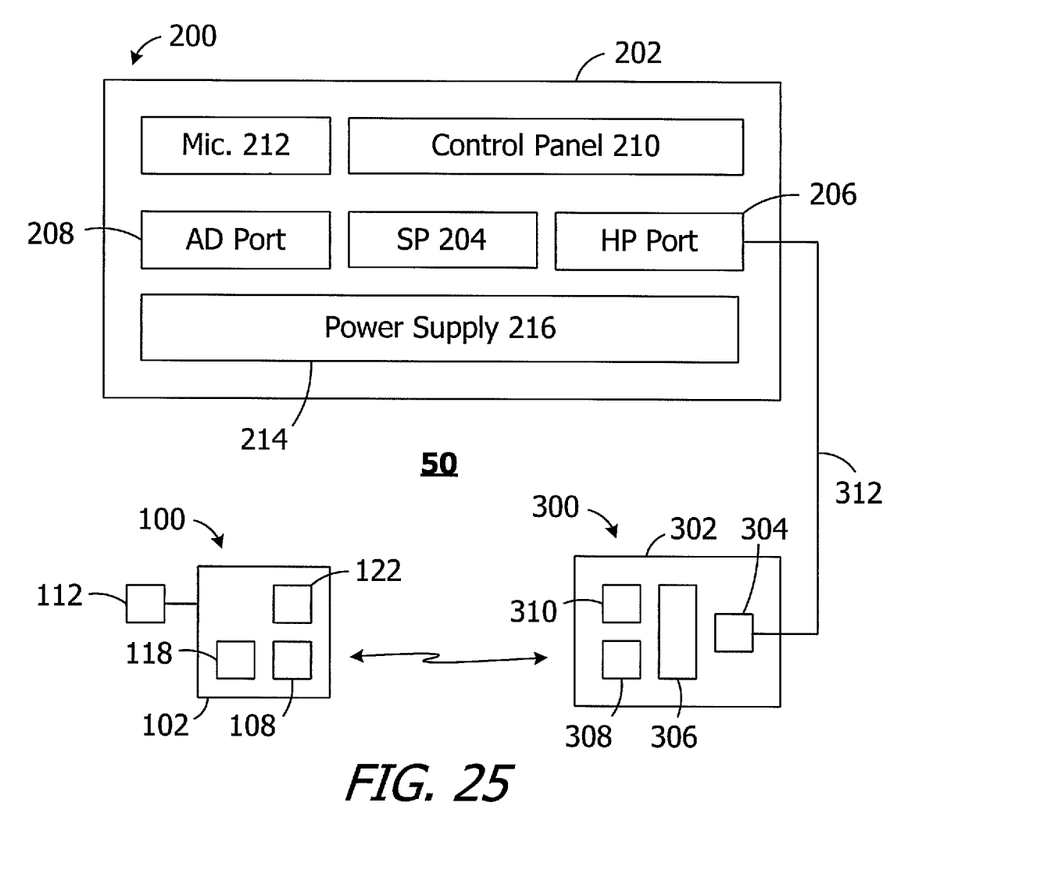
FIG. 25 is a block diagram of a cochlear implant system in accordance with one embodiment of a present invention.

As illustrated in FIG. 25, the exemplary cochlear implant system 50 includes the cochlear implant 100, a sound processor, such as the illustrated body worn sound processor 200 or a behind-the-ear sound processor, and a headpiece 300.

The exemplary body worn sound processor 200 in the exemplary ICS system 50 includes a housing 202 in which and/or on which various components are supported. Such components may include, but are not limited to, sound processor circuitry 204, a headpiece port 206, an auxiliary device port 208 for an auxiliary device such as a mobile phone or a music player, a control panel 210, one or more microphones 212, and a power supply receptacle 214 for a removable battery or other removable power supply 216 (e.g., rechargeable and disposable batteries or other electrochemical cells). The sound processor circuitry 204 converts electrical signals from the microphone 212 into stimulation data. The exemplary headpiece 300 includes a housing 302 and various components, e.g., a RF connector 304, a microphone 306, an antenna (or other transmitter) 308 and a positioning magnet apparatus 310, that are carried by the housing. The magnet apparatus 310 may consist of a single magnet or may consist of one or more magnets and a shim. The headpiece 300 may be connected to the sound processor headpiece port 206 by a cable 312. The positioning magnet apparatus 310 is attracted to the magnet 124 of the cochlear stimulator 100, thereby aligning the antenna 308 with the antenna 108. The stimulation data and, in many instances power, is supplied to the headpiece 300. The headpiece 300 transcutaneously transmits the stimulation data, and in many instances power, to the cochlear implant 100 by way of a wireless link between the antennas. The stimulation processor 118 converts the stimulation data into stimulation signals that stimulate the electrodes 114 of the electrode array 112.

In at least some implementations, the cable 312 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 212 on the sound processor 200, the microphone 306 may be also be omitted in some instances. The functionality of the sound processor 200 and headpiece 300 may also be combined into a single head wearable sound processor. Examples of head wearable sound processors are illustrated and described in U.S. Pat. Nos. 8,811,643 and 8,983,102, which are incorporated herein by reference in their entirety.

It should also be noted that cochlear implants are merely one example of a type of implantable medical device that benefits from the present inventions. Other exemplary implantable medical devices that may be provided with the present resilient mounting tabs, and be disconnected and connected to bone anchors in the manner described above, include, but are not limited to, cardiac pacemakers, defibrillators, recording devices, neuromuscular stimulators drug infusion pumps and deep brain stimulators.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. A method for use with an implantable medical device that is secured to a tissue structure of a patient by an anchor that passes through an aperture in a mounting tab and into the tissue structure, the method comprising the steps of:
   stretching the mounting tab in such a manner that the aperture increases in size while the anchor that passes through the aperture remains in the tissue structure; and
   separating the mounting tab from the anchor by moving the stretched mounting tab in such a manner that the anchor does not extend through the aperture in the mounting tab while the anchor that passes through the aperture remains in the tissue structure.

2. A method as claimed in claim 1, further comprising the step of:
   removing the implantable medical device from the patient after the mounting tab has been separated from the anchor.

3. A method as claimed in claim 2, further comprising the steps of:
   inserting an implantable medical device including a mounting tab with an aperture into the patient;
   stretching the mounting tab in such a manner that the aperture increases in size; and
   connecting the mounting tab to the anchor by moving the stretched mounting tab in such a manner that the anchor extends through the aperture in the mounting tab.

4. A method as claimed in claim 1, wherein the mounting tab defines a first mounting tab, the anchor defines a first anchor, and the implantable medical device includes a second mounting tab that is secured to the tissue structure of the patient by a second anchor that passes through the aperture in the second mounting tab and into the tissue structure, the method further comprising the steps of:
   stretching the second mounting tab in such a manner that the aperture of the second mounting tab increases in size; and
   separating the second mounting tab from the second anchor by moving the stretched second mounting tab in such a manner that the second anchor does not extend through the aperture in the second mounting tab.

5. A method as claimed in claim 1, wherein
   the anchor includes a first portion that extends through the aperture and into the tissue structure and a second portion that is larger than the first portion;
   the entire aperture is between the tissue structure and the second portion prior to the stretching and moving steps; and
   a portion of the aperture is not between the tissue structure and the second portion after the stretching.

6. A method as claimed in claim 1, wherein
   the anchor includes a shank that extends through the aperture and into the tissue structure and a head that is larger than the shank;
   the entire aperture is between the tissue structure and the head prior to the stretching an moving steps; and
   a portion of the aperture is not between the tissue structure and the head after the stretching.

7. A method as claimed in claim 6, wherein
   the shank includes a threaded portion and a non-threaded portion.

8. A method as claimed in claim 7, wherein
   the anchor includes a flange between the threaded portion and the non-threaded portion.

9. A method as claimed in claim 1, further comprising the step of:

allowing the mounting tab to return to an unstretched state after it has been separated from the anchor.

10. A method as claimed in claim 1, wherein the step of stretching the mounting tab comprises stretching the mounting tab in such a manner that the aperture increases in size and the mounting tab does not tear.

11. A method as claimed in claim 1, wherein the implantable medical device comprises a cochlear implant.

12. A method as claimed in claim 1, wherein the tissue structure comprises bone and the anchor comprises a bone anchor.

13. A method as claimed in claim 1, wherein at least a portion of the mounting tab is resilient.

14. A system, comprising:
an anchor having a post and a head that is larger than the post; and
an implantable medical device including
an operative portion, and
at least one mounting tab associated with the operative portion and having an aperture that is configured to receive the post, at least a portion of the mounting tab being resilient and configured to stretch, in a first direction without tearing, from a first size where the aperture is smaller than the anchor head to a second size that is larger than the first size in the first direction and that allows the aperture to fit over the anchor head.

15. A system as claimed in claim 14, wherein the anchor post includes a threaded portion and a non-threaded portion.

16. A system as claimed in claim 15, wherein the anchor includes a flange between the threaded portion and the non-threaded portion.

\* \* \* \* \*